US011793581B2

(12) United States Patent
Itkowitz et al.

(10) Patent No.: US 11,793,581 B2
(45) Date of Patent: *Oct. 24, 2023

(54) SURGICAL SYSTEM WITH OBSTACLE INDICATION SYSTEM

(71) Applicant: INTUITIVE SURGICAL OPERATIONS, INC., Sunnyvale, CA (US)

(72) Inventors: Brandon D. Itkowitz, Sunnyvale, CA (US); Michael L. Hanuschik, Mountain View, CA (US); Paul W. Mohr, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1547 days.

This patent is subject to a terminal disclaimer.

(21) Appl. No.: 15/909,287

(22) Filed: Mar. 1, 2018

(65) Prior Publication Data

US 2018/0185106 A1    Jul. 5, 2018

Related U.S. Application Data

(63) Continuation of application No. 14/659,833, filed on Mar. 17, 2015, now Pat. No. 9,918,800.

(Continued)

(51) Int. Cl.
*A61B 34/30*    (2016.01)
*A61B 90/35*    (2016.01)
(Continued)

(52) U.S. Cl.
CPC .............. *A61B 34/30* (2016.02); *A61B 90/35* (2016.02); *A61B 5/0017* (2013.01); *A61B 90/30* (2016.02);
(Continued)

(58) Field of Classification Search
CPC ......... A61B 34/30; A61B 90/35; A61B 90/30; A61B 5/0017; A61B 2017/00075; A61B 2560/02; A61B 2560/0266
See application file for complete search history.

(56) References Cited

U.S. PATENT DOCUMENTS 5,598,164 A    1/1997    Reppas et al.
6,272,368 B1 *    8/2001    Alexandrescu ........ A61B 6/488
600/407

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Peter Luong
(74) *Attorney, Agent, or Firm* — JONES ROBB, PLLC

(57) ABSTRACT

A patient side cart for a teleoperated surgical system may comprise a column extending from a base, the column having a first end connected to the base and a second end opposite the first end. The patient side cart may further include a surgical instrument manipulator arm coupled proximate the second end of the column, and an obstacle indication system comprising an illumination source mounted on the patient side cart at a height above a location the surgical instrument manipulator arm is coupled to the second end of the column, the height being measured in a direction the column extends from the base.

22 Claims, 10 Drawing Sheets

Related U.S. Application Data

(60) Provisional application No. 61/954,273, filed on Mar. 17, 2014.

(51) Int. Cl.
 *A61B 17/00* (2006.01)
 *A61B 90/30* (2016.01)
 *A61B 5/00* (2006.01)

(52) U.S. Cl.
 CPC . *A61B 2017/00075* (2013.01); *A61B 2560/02* (2013.01); *A61B 2560/0266* (2013.01)

(56) References Cited

U.S. PATENT DOCUMENTS

| | | | |
|---|---|---|---|
| 7,046,765 B2 * | 5/2006 | Wong | A61N 5/10 378/117 |
| 9,918,800 B2 | 3/2018 | Itkowitz et al. | |
| 2005/0232397 A1 | 10/2005 | Atzinger et al. | |
| 2008/0144778 A1 | 6/2008 | Sonani | |
| 2010/0204713 A1 | 8/2010 | Ruiz | |
| 2013/0325031 A1 | 12/2013 | Schena et al. | |
| 2013/0325033 A1 | 12/2013 | Schema et al. | |
| 2014/0316654 A1 | 10/2014 | Griffiths et al. | |

\* cited by examiner

SURGICAL SYSTEM WITH OBSTACLE INDICATION SYSTEM

CROSS-REFERENCE TO RELATED APPLICATIONS

This application is a continuation application of U.S. application Ser. No. 14/659,833, filed Mar. 17, 2015, which claims priority to U.S. Provisional Application No. 61/954,273, filed Mar. 17, 2014, each of which is incorporated by reference herein in its entirety.

TECHNICAL FIELD

Aspects of the present disclosure relate to surgical systems including obstacle indication devices, and related systems and methods.

BACKGROUND

A teleoperated (robotic) surgical system may include a surgeon console at which a surgeon may input commands to control one or more teleoperated surgical instruments mounted at a patient side cart during a surgical procedure. The patient side cart may be moved about an operating room, such as to position the patient side cart proximate a patient for the surgical procedure. One consideration when moving the patient side cart is whether the patient side cart can collide with an object, such as an object hanging from the ceiling of an operating room. Such collisions could also occur when moving components of the cart, such as when moving setup joints of the cart to prepare the cart for a surgical procedure or moving the cart after a surgical procedure has been completed.

While patient side carts have been effective for being moved from one location to another, further improvements upon patient side carts are desirable. For example, it may be desirable to provide patient side carts with devices to facilitate recognition of obstacles that the patient side cart may collide with when the cart is moved from one location to another or when components of the cart are being positioned.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a patient side cart for a teleoperated surgical system may comprise a base, a column connected to the base, a boom connected to the column, a surgical instrument manipulator arm connected to the boom, and an obstacle indication system comprising an illumination source that directs light in a path of the boom.

In accordance with another exemplary embodiment, a method of providing obstacle indication via a patient side cart of a teleoperated surgical system including a base, a column connected to the base, and a boom connected to the column, may comprise directing light emitted from an illumination source located in the boom. The light may be directed onto an object in a path of the boom to indicate that the object is located in a path of the boom.

In accordance with another exemplary embodiment, a method of determining a predetermined height to be stored in a patient side cart for a teleoperated surgical system may comprise orienting the patient side cart to place an object in a path of the patient side cart. The method may further comprise illuminating the object in the path of the patient side cart. The method may further comprise storing a current height of the patient side cart as the predetermined height.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

DETAILED DESCRIPTION

Figure 1:
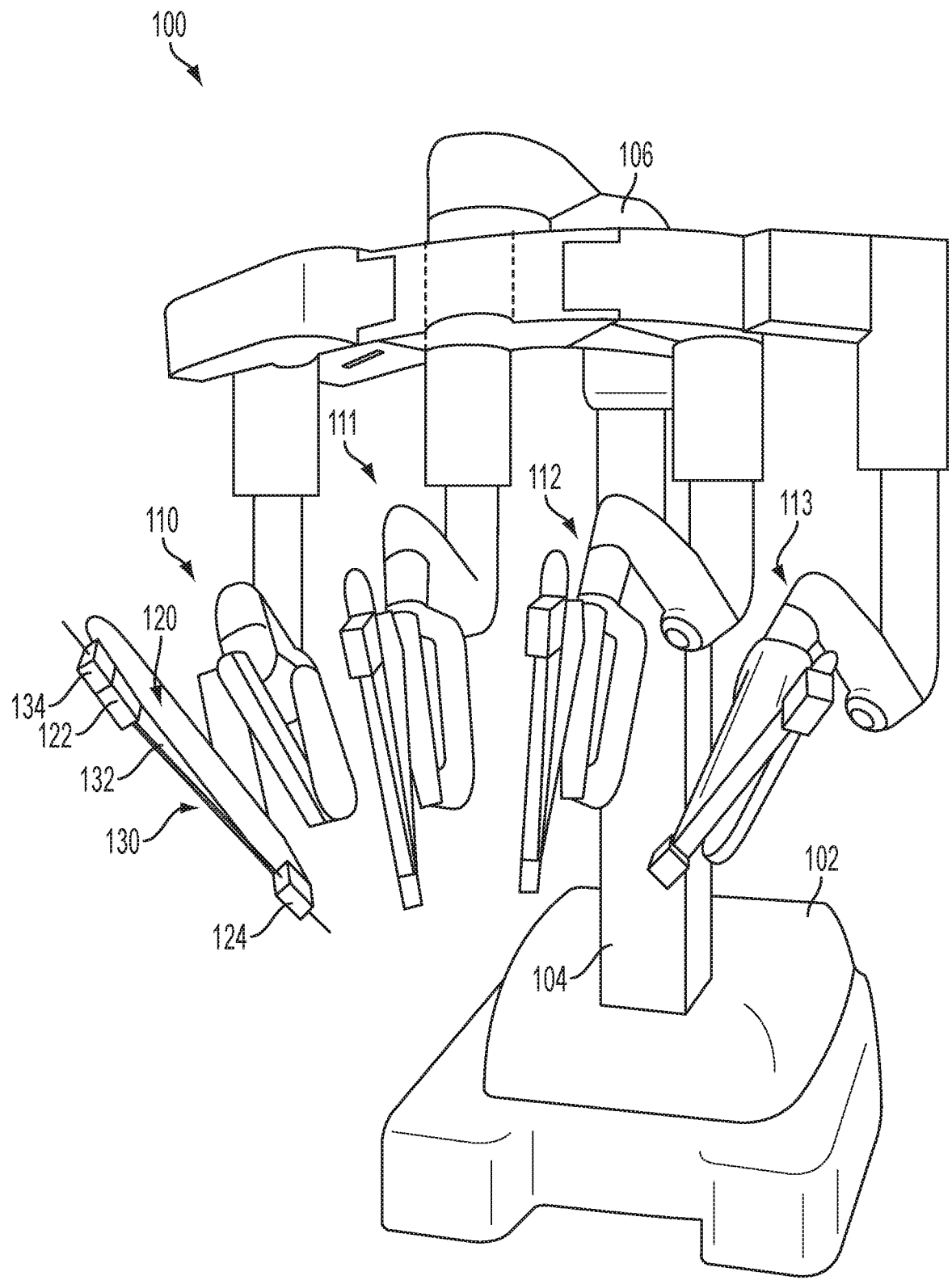
FIG. 1 is a perspective schematic view of a patient side cart, according to an exemplary embodiment.

This description and the accompanying drawings that illustrate exemplary embodiments should not be taken as limiting. Various mechanical, compositional, structural, electrical, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the disclosure or claims. For example, spatially relative terms—such as "beneath", "below", "lower", "above", "upper", "proximal", "distal", and the like—may be used to describe one element's or feature's relationship to another element or feature as illustrated in the orientation of the figures. These spatially relative terms are intended to encompass different positions (i.e., locations) and orientations (i.e., rotational placements) of a device in use or operation in addition to the position and orientation shown in the figures. For example, if a device in the figures is inverted, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. The relative proximal and distal directions of surgical instruments are labeled in the figures.

The present disclosure contemplates patient side carts for teleoperated surgical systems that are equipped to facilitate indication of an obstacle the patient side cart has the potential to collide with as the patient side cart is being moved from one location to another, such as when the cart is being moved within an operating room. Devices and systems in accordance with the present disclosure may assist a user maneuvering the cart by indicating the presence of an object within the height of the patient side cart. Thus, the user may be warned of the potential for a collision with the object and be prompted to take corrective action before a collision occurs.

Various exemplary embodiments of the present disclosure contemplate a patient side cart for a teleoperated surgical system comprising a base, a column connected to the base, a boom connected to the column, a manipulator arm connected to the boom to support a surgical instrument, and an obstacle indication recognition system comprising an illumination source that directs light unto an object in a path of the boom. The illumination source may be, for example, a laser. The laser may project light spanning an angular range, such as, for example, from about 45 degrees to about 135 degrees. The illumination source may be automatically activated upon movement of the patient side cart from one location to another. The column can be extended and retracted to respectively raise and lower the boom and the illumination source may be automatically activated in response to extending or retracting the column. The patient side cart may include a non-volatile memory to store a predetermined height that corresponds to a height of an object with which the boom could collide. The illumination source is automatically activated when a height of the patient side cart equals or exceeds the predetermined height stored in the memory. The illumination source may be automatically activated when a height of the patient side cart equals or exceeds a predetermined height threshold that is a fraction of the predetermined height. The predetermined height threshold may be about 80% of the predetermined height stored in the memory. The obstacle indication system may detect the object in the path of the patient side cart and automatically provides feedback upon detection of the object. The illumination device may be a lidar device to facilitate detecting the objecting and automatically providing feedback.

Various exemplary embodiments of the present disclosure further contemplate a method of providing obstacle indication via a patient side cart of a teleoperated surgical system including a base, a column connected to the base, and a boom connected to the column, the method comprising directing light emitted from an illumination source located in the boom, with the light being directed onto an object in a path of the boom to notify a user that the object is located in a path of the boom. The illumination source may be automatically activated upon movement of the patient side cart from one location to another. The illumination source may be automatically activated in response to extending or retracting the column. The illumination source may be automatically activated when a height of the patient side cart equals or exceeds a predetermined height stored in a non-volatile memory of the patient side cart, with the predetermined height corresponding to a height of the object. The illumination source device may be automatically activated when a height of the patient side cart equals or exceeds a predetermined height threshold based on a predetermined height stored in the memory, with the predetermined height threshold being a fraction of the predetermined height. The obstacle indication system may detect the object in the path of the patient side cart and automatically provide feedback upon detection of the object.

Various exemplary embodiments of the present disclosure also contemplate a method of determining a predetermined height to be stored in a patient side cart for a teleoperated surgical system. In such methods, a patient side cart may be oriented to place an object in a path of the patient side cart, an object in the path of the patient side cart may be illuminated, and the current height of the patient side cart may be stored as the predetermined height. The orienting and the illuminating may be repeated to determine heights of a plurality of objects. When heights have been determined for a plurality of objects, the patient side cart may select only the lowest height from amongst the various heights determined for the plurality of objects.

Referring now to FIG. 1, an exemplary embodiment of a patient side cart 100 of a teleoperated surgical system is shown. As those having ordinary skill in the art are familiar with, a teleoperated surgical system may further include a surgeon console (not shown) for receiving input from a user to control instruments of patient side cart 100, as well as an auxiliary control/vision cart (not shown), as described in for example, U.S. Pub. No. US 2013/0325033, entitled "Multi-Port Surgical Robotic System Architecture" and published on Dec. 5, 2013, and U.S. Pub. No. U.S. 2013/0325031, entitled "Redundant Axis and Degree of Freedom for Hardware-Constrained Remote Center Robotic Manipulator" and published on Dec. 5, 2013, each of which is hereby incorporated by reference in its entirety. By way of non-limiting example, a teleoperated surgical system of the type contemplated by the present disclosure includes a da Vinci® Surgical System available from Intuitive Surgical, Inc.

Patient side cart 100 may include a base 102, a main column 104, and a main boom 106 connected to main column 104. Patient side cart 100 also may include a plurality of manipulator arms 110, 111, 112, 113, which may each be connected to main boom 106. Portions of manipulator arms 110, 111, 112, 113 may include an instrument mount portion 120 to which an instrument 130 may be mounted, as illustrated for manipulator arm 110. Manipulator arms 110, 111, 112, 113 may be manipulated during a surgical procedure according to commands provided by a user at the surgeon console. In an exemplary embodiment, signal(s) or input(s) transmitted from a surgeon console may be transmitted to the control/vision cart, which may interpret the input(s) and generate command(s) or output(s) to be transmitted to the patient side cart 100 to cause manipulation of an instrument 130 (only one such instrument being mounted in FIG. 1) and/or portions of manipulator arm 110 to which the instrument 130 is coupled at the patient side cart 100.

Instrument mount portion 120 may comprise an actuation interface assembly 122 and a cannula mount 124, with a shaft 132 of instrument 130 extending through cannula mount 124 (and on to a surgery site during a surgical procedure) and a force transmission mechanism 134 of instrument connecting with the actuation interface assembly 122, according to an exemplary embodiment. Cannula mount 124 may be configured to hold a cannula (not shown) through which shaft 132 of instrument 130 may extend to a surgery site during a surgical procedure. Actuation interface assembly 122 may contain a variety of mechanisms that are controlled to respond to input commands at the surgeon console and transmit forces to the force transmission mechanism 134 to actuate instrument 130.

Although the exemplary embodiment of FIG. 1 shows an instrument 130 attached to only manipulator arm 110 for ease of viewing, an instrument may be attached to any and each of manipulator arms 110, 111, 112, 113. An instrument 130 may be a surgical instrument with an end effector or may be a camera instrument or other sensing instrument utilized during a surgical procedure to provide information, (e.g., visualization, electrophysiological activity, pressure, fluid flow, and/or other sensed data) of a remote surgical site. In the exemplary of FIG. 1, either a surgical instrument with an end effector or a camera instrument may be attached to and used with any of manipulator arms 110, 111, 112, 113. However, the embodiments described herein are not limited to the exemplary embodiment of FIG. 1 and various other teleoperated surgical system configurations may be used with the exemplary embodiments described herein.

Figure 2:
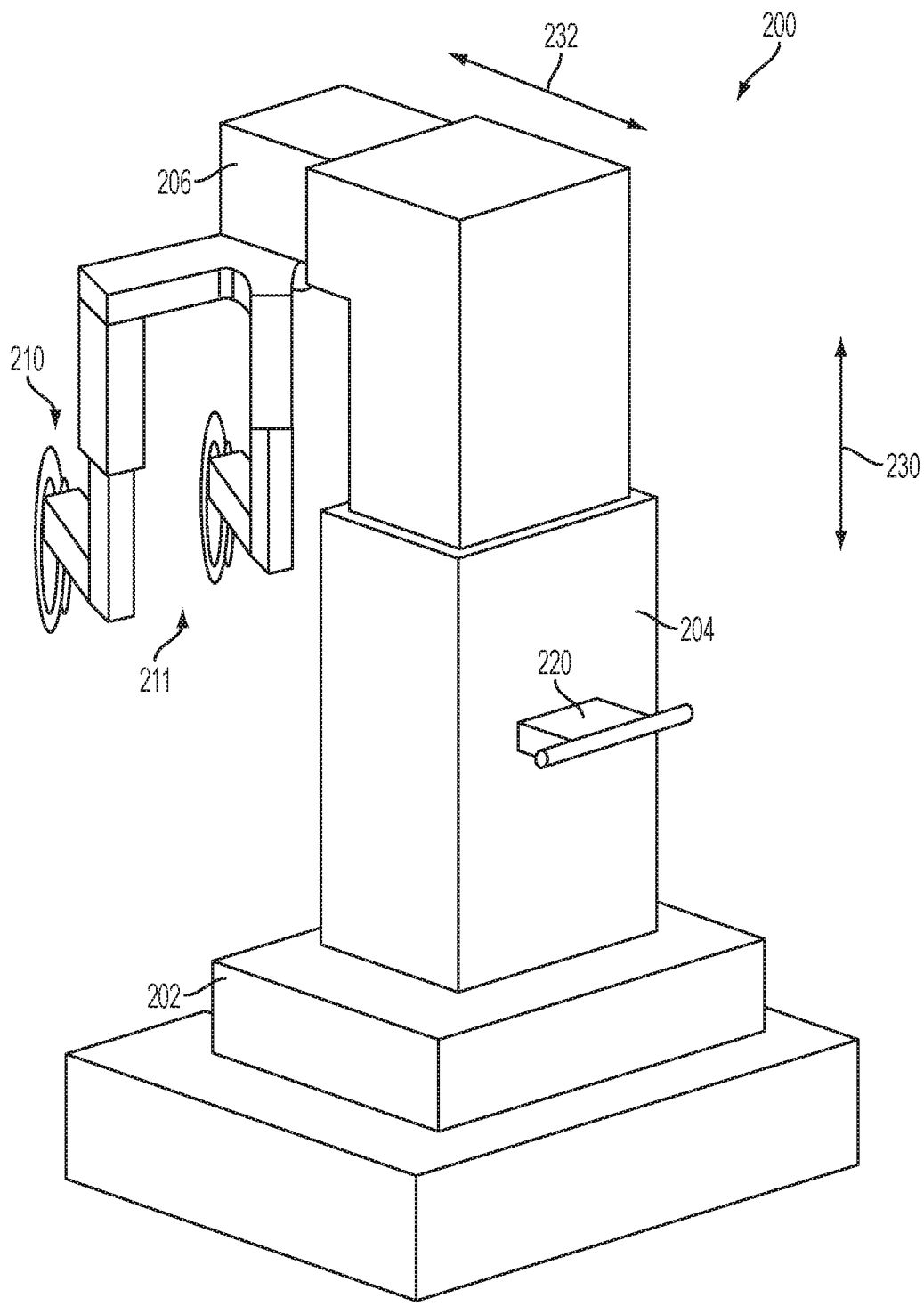
FIG. 2 is another perspective schematic view of a patient side cart including a steering interface, according to an exemplary embodiment.

A patient side cart may include one or more device(s) to control movement of the patient side cart from one location to another, such as when moving the patient side cart about an operating room to prepare for a surgical procedure or after a surgical procedure has been completed. Turning to FIG. 2, a patient side cart 200 is schematically shown. As in FIG. 1, patient side cart 200 includes a base 202, a column 204, and a boom 206 connected to column 204. Patient side cart 200 may include a plurality of manipulator arms, with manipulator arms 210 and 211 being depicted. Although only two manipulator arms 210 and 211 are depicted in FIG. 2, patient side cart 200 may include more manipulator arms, as discussed above with regard to patient side cart 100.

Patient side cart 200 may include a steering interface 220 for a user to drive patient side cart 200 from one location to another, according to an exemplary embodiment. Steering interface 220 may be configured, for example, according to the various exemplary embodiments described in U.S. application Ser. No. 14/208,663 entitled "Surgical Patient Side Cart with Steering Interface," filed on Mar. 13, 2014, now U.S. Pat. No. 9,308,937, which is hereby incorporated by reference in its entirety. As described in U.S. application Ser. No. 14/208,663, steering interface 220 may be used to detect forces applied by a user to the steering interface 220, which in turn may issue a signal to a controller of a motorized drive system of patient side cart 200, which causes the patient side cart 200 to be driven and steered in a desired manner. As shown in the example of FIG. 2, steering interface 220 may be attached to a rear of a patient side cart 200, with manipulator arms 210 and 211 being located on a front end of patient side cart 200. However, the exemplary embodiments described herein are not limited to a patient side cart 200 with a steering interface 220 attached to a rear, and the steering interface 220 may instead be mounted on other portions of a patient side cart 200, such as a front or side of the patient side cart 200. Nor is a patient side cart in accordance with the present disclosure limited to including a motorized drive control system, as set forth in U.S. application Ser. No. 14/208,663.

Patient side cart 200 may further include controls to modify the configuration of patient side cart 200, such as to setup patient side cart 200 for a surgical procedure. According to an exemplary embodiment, column 204 may be extendable and retractable along directions 230 in FIG. 2. For example, column 204 may include telescoping sections that can be extended and retracted relative to one another. Column 204 may be extended and retracted along directions 230 to set patient side cart 200 at a desired height during a surgical procedure, such as to adjust the height of column 204, boom 206, and manipulator arms 210 and 211 to a desired height relative to patient. In addition, boom 206 may be extended and retracted along directions 232 in FIG. 2, according to an exemplary embodiment. For example, boom 206 may include telescoping sections that can be extended and retracted relative to one another. Boom 206 may be extended and retracted along directions 232 to position boom 206 and manipulator arms 210 and 211 at a desired location relative to a patient located next to patient side cart 200. Control inputs to extend or retract column 204 and/or boom 206 may be located on, for example, steering interface 220, according to an exemplary embodiment, although other placements are contemplated as within the scope of the present disclosure and claims.

Figure 3:
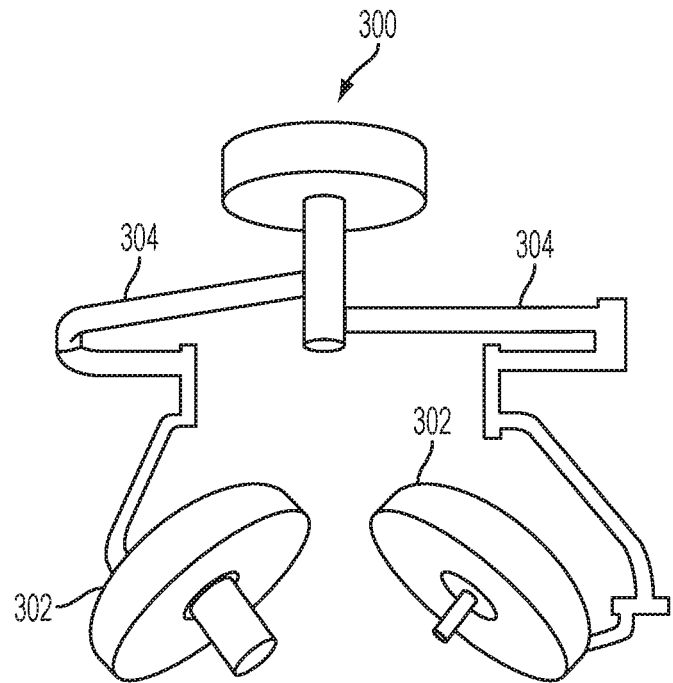
FIG. 3 depicts a ceiling mounted fixture, according to an exemplary embodiment.
Figure 4:
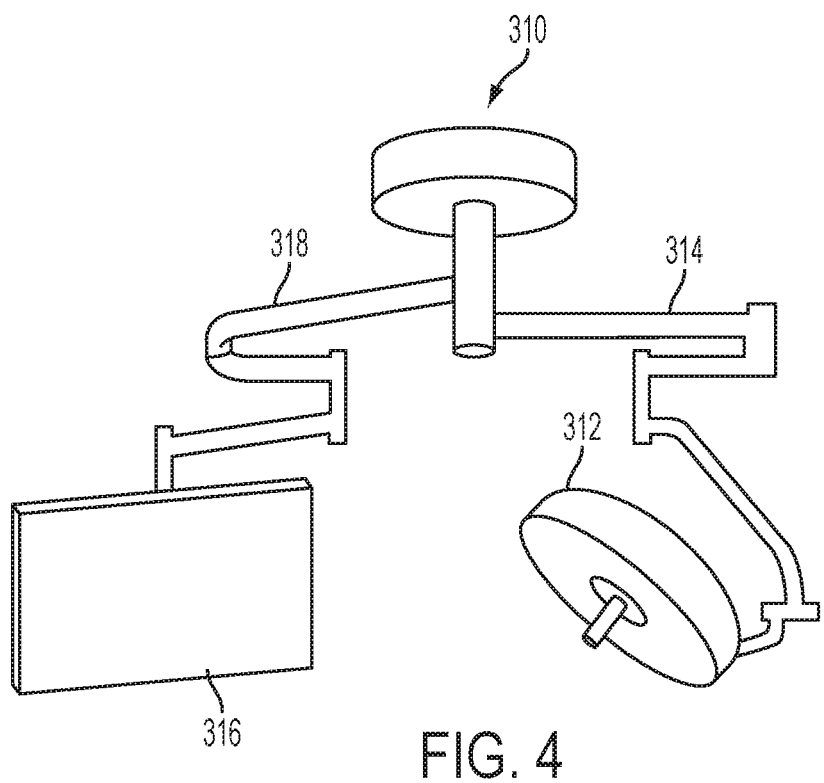
FIG. 4 depicts a ceiling mounted fixture, according to another exemplary embodiment.

As discussed above, a patient side cart may be moved from one location to another or the patient side cart may be reconfigured (e.g., by extending/retracting column 204 and/or boom 206 in FIG. 2) to prepare for a surgical procedure or to move the cart after a surgical procedure has been completed. It is desirable for a user to be notified of obstacles present in the room where the patient side cart is located that pose a collision potential when moving or reconfiguring the patient side cart. Turning to FIG. 3, an exemplary embodiment of one type of obstacle is shown, which is a ceiling-mounted light fixture 300. Light fixture 300 may include lights 302 mounted upon arms 304 to permit lights 302 to be positioned in various configurations. Because light fixture 300 may hang from a ceiling of an operating room, light fixture 300 may be an obstacle that a patient side cart may collide with when the patient side cart is being moved from one location to another or when the cart is being reconfigured. FIG. 4 depicts an exemplary embodiment of another possible obstacle, which is a fixture 310 including a light 312 mounted on an arm 314 and a monitor 316 mounted on an arm 318. Other obstacles (e.g., other ceiling-mounted objects, wall-mounted objects, and other operating room obstacles familiar to one of ordinary skill in the art) may be considered when moving or reconfiguring a patient side cart.

Figure 5:
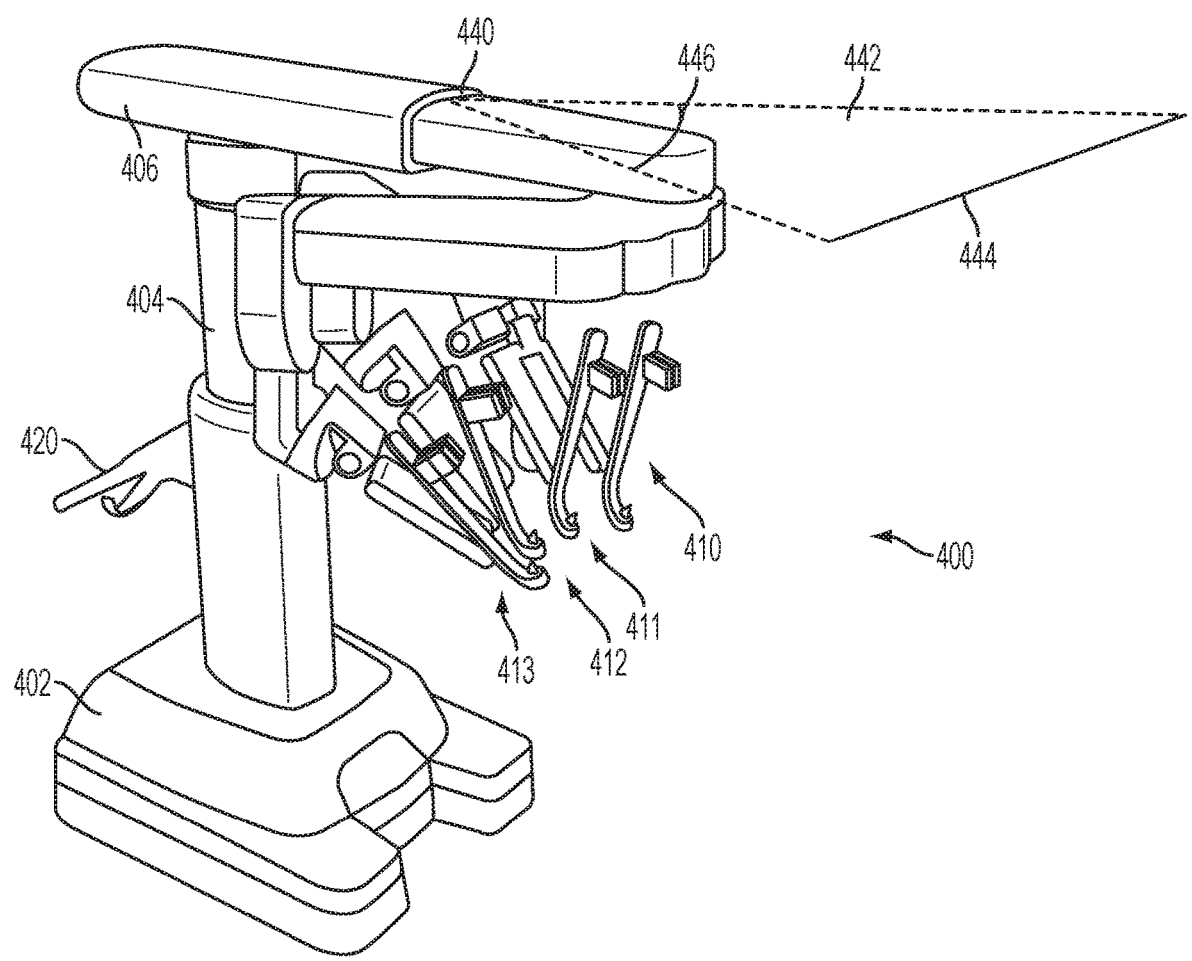
FIG. 5 is a perspective view of a patient side cart including an obstacle recognition device, according to an exemplary embodiment.
Figure 6:
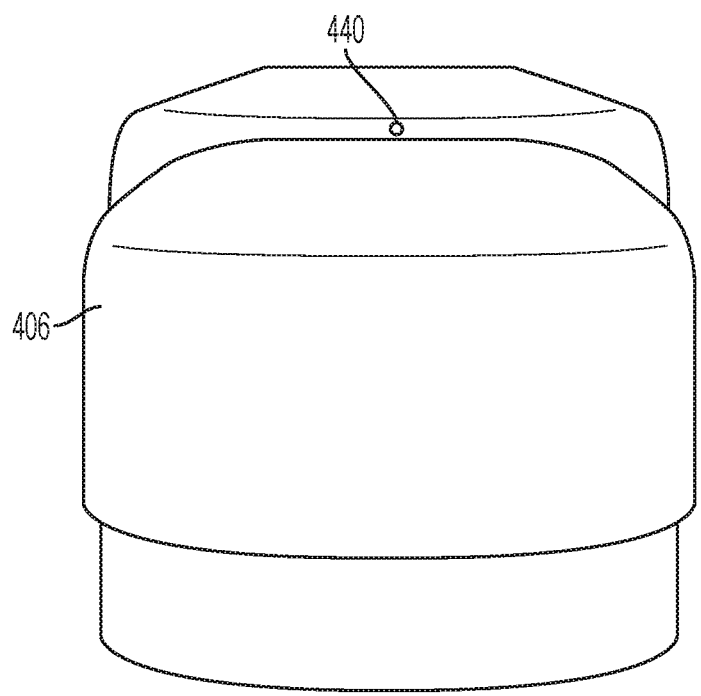
FIG. 6 is an end view of the boom of the patient side cart of FIG. 5.

To minimize or prevent collisions with obstacles, a patient side cart may be provided with the ability to provide notification to a user of obstacles that the cart has a potential to collide with. Turning to FIG. 5, a patient side cart 400 is schematically shown that includes a base 402, a column 404, a boom 406 connected to column 404, manipulator arms 410-413, and steering interface 420. Patient side cart 400 may be configured according to the exemplary embodiments of FIGS. 1 and 2. Patient side cart 400 may include a device to facilitate indication of the presence of obstacle(s). According to an exemplary embodiment, boom 406 may include a device to facilitate recognition of an obstacle that lies within a path of boom 406. In the various exemplary embodiments described herein, the path may be defined, for example, by a direction of movement of patient side cart 400. Boom 406 may include the device because boom 406 is the highest portion of patient side cart 400 with respect to a vertical distance from a ground surface, in various exemplary embodiments. However, the device could be located in other components of a patient side cart. As shown in FIG. 6, which depicts an end view of boom 406, boom 406 may include a laser 440 that emits light to illuminate an obstacle located at a height within a collision path of patient side cart 400. Other devices to facilitate recognition of an obstacle besides a laser, such as other illumination devices, are contemplated by the various exemplary embodiments described herein, some of which will be described below.

Laser 440 may be used to facilitate recognition of an obstacle by illuminating light upon an object (not shown in FIG. 5). The object may be, for example, fixtures 300 or 310 shown in FIGS. 3 and 4 or other objects located in an operating room that one of ordinary skill in the art is familiar with, which may be located at a height within a collision path of patient side cart 400, such as when cart 400 is moved from one location to another or is reconfigured by moving column 404 and/or boom 406. As shown in FIG. 5, laser 440 may emit light 442 that can be projected onto an object located in front of boom 406. When this occurs, the illuminated light upon the object indicates that the object is an obstacle with which patient side cart 400 may collide. Thus, a user may see the light 442 illuminated upon the object and recognize that the object is an obstacle with which patient side cart 400 could collide, which can allow the user to take corrective action to avoid the obstacle.

A laser used to facilitate recognition of an obstacle may emit light over an area to facilitate recognition of objects. As shown in the exemplary embodiment of FIG. 5, laser 440 may emit light 442 spanning an angular range, such as in a fan or wedge shape, so that light 442 will illuminate any objects located within area illuminated by light 442. According to an exemplary embodiment, the total angular range for the fan shape of light 442 for angle 446 may range from, for example, about 45 degrees to about 135 degrees. According to another exemplary embodiment, the fan shape of light 442 may have an angle 446 of, for example, about 90 degrees.

Turning back to FIG. 5, because light 442 is emitted over an area, light 442 may project a pattern onto an object illuminated by light 442. According to an exemplary embodiment, laser 440 may project light 442 in a linear pattern 444, as shown in FIG. 5, such as when light 442 is projected in a fan shape. Thus, an object located within the projected fan shape of light 442 will have at least a portion of pattern 444 projected onto the object, permitting a user to see the portion of pattern 444 on the object and recognize the object as an obstacle. Pattern 444 may be a continuous pattern, as shown in the exemplary embodiment of FIG. 5. The various exemplary embodiments described herein are not limited to a continuous pattern but instead include non-continuous patterns (e.g., a discontinuous series of shapes, such as circles or other shapes), which may be arranged in a linear pattern or other pattern familiar to one of ordinary skill in the art.

Further, a color of light 442 projected by laser 440 may be selected to facilitate viewing of pattern 444 by a user. According to an exemplary embodiment, light 442 may have, for example, a green color, which can provide enhanced contrast on dark surfaces. The various exemplary embodiments described herein are not limited to green laser light and may instead use other colors, such as, for example, red, blue, or other laser light colors familiar to one of ordinary skill in the art.

Figure 7:
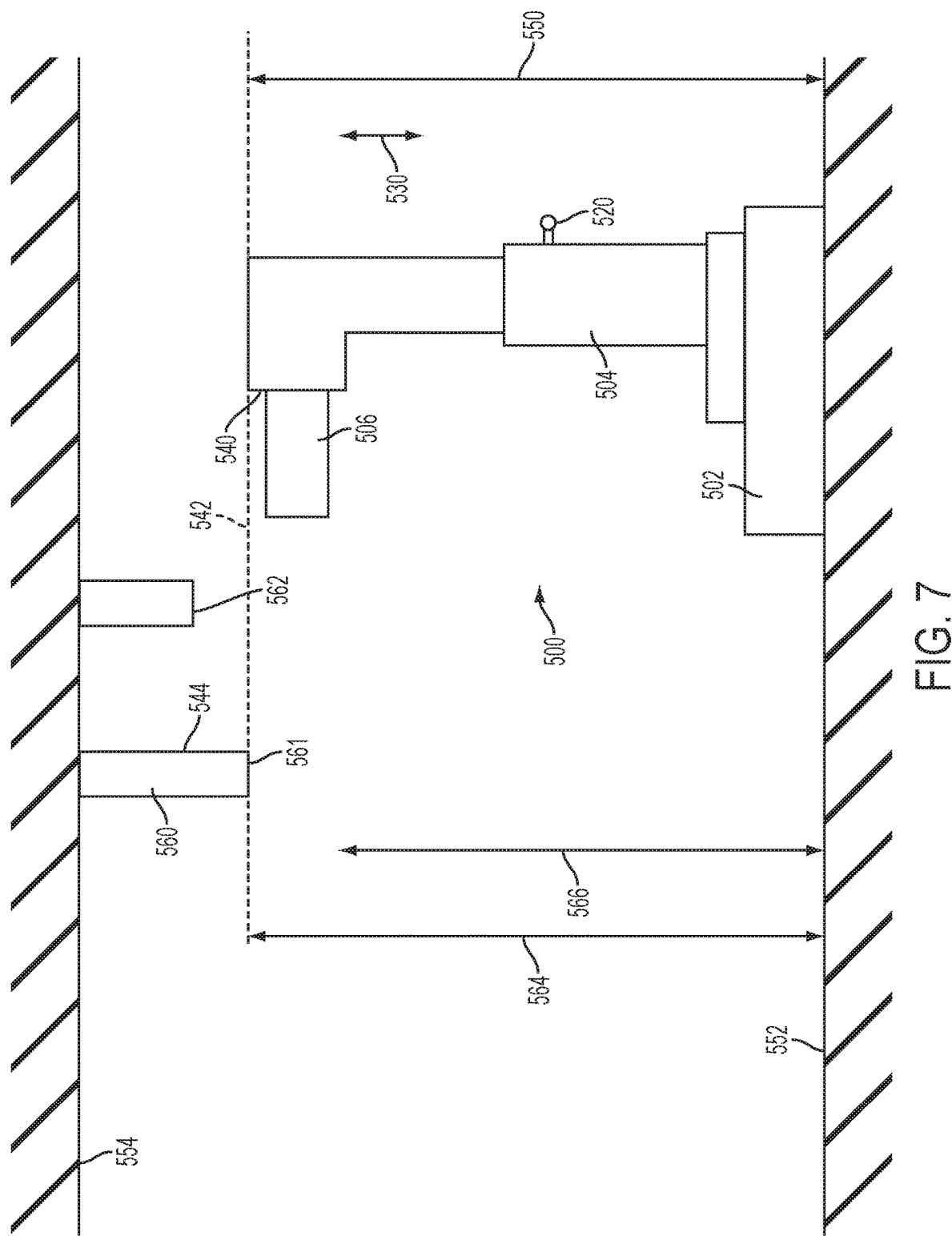
FIG. 7 is a schematic side view of a patient side cart in a room with objects, according to an exemplary embodiment.

Use of a device to facilitate indication of the presence of an obstacle will now be discussed with reference to FIG. 7. A patient side cart 500 is schematically shown and includes a base 502, a column 504, a boom 506 connected to column 504, and a steering interface 520. Patient side cart 500 may be configured according to the exemplary embodiments of FIGS. 1, 2, and 5 and may include manipulator arms (not shown in FIG. 7 for ease of illustration). Patient side cart 500 may include a device to facilitate recognition of an obstacle, such as, for example, a laser 540. As discussed above with regard to the exemplary embodiment of FIGS. 5 and 6, laser 540 may emit light 542 to illuminate an object 560 in the path of cart 500, such as by projecting light 544, which may be in a pattern, onto object 560. Further, light 542 may be emitted in a direction substantially parallel to ground surface 552. For instance, light 542 may be emitted in a direction having an angle of about +/−2° or less with respect to ground surface 552. Objects 560 and 562, may be, for example, fixtures 300 or 310 shown in FIGS. 3 and 4 or other objects located in an operating room that one of ordinary skill in the art is familiar with.

A device to facilitate indication of the presence of an obstacle may be activated when a patient side cart is moved from one location to another. When a user utilizes steering interface 520 to move patient side cart 500 to another location, a device to facilitate recognition of an obstacle may be automatically activated, according to an exemplary embodiment. In the exemplary embodiment of FIG. 7, laser 540 may be automatically activated, such as by a controller receiving drive commands input by a user at steering interface 520, to illuminate any obstacles in a path of cart 500 with light 542 once cart 500 is moving. For instance, when patient side cart 500 is driven on a ground surface 552 in FIG. 7 from one location to another, objects 560 and 562 hanging from ceiling 554 may be obstacles that cart 500 could collide with. In the exemplary embodiment of FIG. 7, boom 506 of patient side cart 500 is at a vertical height 550 that is below object 562, permitting boom 506 to pass beneath object 562. As a result, light 542 emitted by laser 540 does not illuminate object 562. In contrast, the vertical height 550 of boom 506 corresponds to the vertical height 564 of a portion of object 560, which can lead to a collision between boom 506 and object 560. However, light 542 emitted from laser 540 projects onto object 560 so a user of patient side cart may recognize that object 560 is an obstacle with which cart 500 has the potential to collide when moving cart across ground surface 552. Thus, a user may see light 544 projected onto object 560, recognize object 560 is an obstacle, and take corrective action (e.g., driving cart 500 around object 560 to avoid a collision).

According to an exemplary embodiment, a predetermined height may be programmed into patient side cart 500 and the device to facilitate recognition of an obstacle may be activated when height 550 of cart 500 is at or above the predetermined height. The predetermined height may be, for example, stored in a memory accessible by the controller receiving input commands from steering interface 520. According to an exemplary embodiment, the memory may be a non-volatile memory, such as, for example, programmable read-only memory (PROM), erasable PROM (EPROM), and electrically EPROM (EEPROM), and flash memory. The predetermined height may be, for example, a height corresponding to a vertical height of an object from a ground surface (e.g., height 564 to object 560), which may be determined in advance. An exemplary embodiment of determining such a height to be stored in a patient side cart will be discussed below. When the vertical height 550 of boom 506 is below the predetermined height, the device to facilitate recognition of an obstacle (e.g., laser 540) may remain deactivated. For example, the controller does not activate laser 540 because the controller determines that vertical height 550, which may be associated with controls to raise and lower boom 506 (e.g., by extending or retracting column 504) along directions 530, is less than the predetermined height.

According to an exemplary embodiment, an obstacle indication system may be activated when a vertical height of a patient side cart is at or above a predetermined threshold relative to a predetermined height. The predetermined height may be stored, for example, in a non-volatile memory accessible by a controller and may be a portion of a vertical height for a portion of an object from a ground surface. By determining whether a patient side cart height is above the threshold instead of the predetermined height itself, a factor of safety is provided when determining whether or not to activate the obstacle recognition system. Thus, instead of determining whether vertical height 550 of patient side cart 500 is at or above the predetermined height, it is determined whether vertical height 550 is at or above a predetermined threshold. When vertical height 550 of patient side cart 500 is at or above the predetermined threshold, cart 500 may provide feedback to a user notifying that the threshold has been reached. The feedback may be, for example, visual and/or audio feedback providing notification that the threshold has been reached and caution should be exercised. According to an exemplary embodiment, the notification may be canceled by a user, such as by using a control on steering interface 520. According to another exemplary embodiment, when threshold has been reached, the controller to drive patient side cart 500 may prevent driving of cart 500, such as via steering interface 520, until the user has acknowledged or overridden the notification of the threshold being reached.

According to an exemplary embodiment, the predetermined threshold may be a fraction of the predetermined height. In the exemplary embodiment of FIG. 7, the threshold may correspond to vertical height 566, which is a fraction of vertical height 564 for object 560, which has been stored as the predetermined height. Thus, whenever the controller of patient side cart 500 determines that vertical height 550 of cart 500 is at or above the threshold (e.g., vertical height 566) the controller activates the obstacle indication system (e.g., laser 540). According to an exemplary embodiment, the threshold (e.g., vertical height 566) may be determined by setting the threshold at about 80% of the predetermined height (e.g., vertical height 564). According to another exemplary embodiment, the threshold may be about 90% of the predetermined height.

According to an exemplary embodiment, patient side cart 500 may include a safety measure that permits laser 540 to be activated only when vertical height 550 is above a typical eye level of a person. For instance, the controller may permit the laser to be activated only when vertical height 550 is above, for example, about 80 inches. This safety measure may be used with the various exemplary embodiments described herein. When laser 540 is prevented from being activated by the safety measure, feedback (e.g., a visual and/or audio notification) may be issued to notify the user that the laser 540 cannot be activated due to the vertical height 550 of boom 506, according to an exemplary embodiment.

When vertical height 550 of patient side cart 500 is at or above the predetermined threshold, cart 500 may provide feedback to a user notifying that the threshold has been reached. The feedback may be, for example, visual and/or audio feedback providing notification that the threshold has been reached and caution should be exercised. According to an exemplary embodiment, the notification may be canceled by a user, such as by using a control on steering interface 520. According to another exemplary embodiment, when threshold has been reached, driving patient side cart 500 may be prevented, such as via steering interface 520 and a motorized drive control system, until the user has acknowledged or overridden the notification of the threshold being reached.

As discussed above, an obstacle indication system may be activated during movement of a patient side cart from one location to another. According to an exemplary embodiment, the system may be activated when raising a boom, such as raising boom 506 of patient side cart 500 (e.g., by extending column 504) along direction 530 in FIG. 7. The obstacle indication system may be activated during movement of boom 506 so a user may be notified whether or not boom 506 has been raised to the height of an object, such as object 560 or 562 installed to ceiling 554, with which boom 506 could collide before moving patient side cart 500. According to an exemplary embodiment, when boom 506 is being raised, the obstacle recognition system (e.g., laser 540) may be automatically activated once the controls to raise or lower boom 506 have been activated. According to another exemplary embodiment, such activation can occur once the boom has been raised to a vertical height at or above a predetermined height (e.g., a previously stored height, as discussed in the exemplary embodiments above). According to another exemplary embodiment, the obstacle indication system may be activated once the boom has been raised to a vertical height at or above a threshold, which may be a fraction of a stored predetermined height, as discussed in the exemplary embodiments above.

According to an exemplary embodiment, patient side cart 500 may be programmed to have a maximum height threshold for cart 500. For example, a predetermined height threshold (which may correspond to, for example, a vertical height 564 of object 560 or vertical height 566, which is a fraction of vertical height 564 for object 560) may be stored in patient side cart 500 and set as the maximum vertical height 550 of boom 506. Thus, when boom 506 is raised by extending column 504 along direction 530, a controller may prevent raising boom 506 further along direction 530 when the maximum height (e.g., the predetermined height or threshold) has been reached. Feedback (e.g., visual and/or audio notification) may be provided to a user notifying the user that the maximum height has been reached, which the user may override, if desired. Exemplary embodiments for setting a maximum height and limiting movement of a patient side cart relative to the maximum height are discussed in U.S. Provisional Patent Application No. 61/942,347, filed on Feb. 20, 2014, which is hereby incorporated by reference in its entirety. Further, a predetermined minimum height threshold may be programmed into a patient side cart, according to an exemplary embodiment. A minimum patient side cart height may be, for example, about 90 inches. If a user attempts to lower boom 506 by retracting column 504 along direction 530 below the predetermined minimum height threshold, the movement may be stopped and feedback provided to the user, which the user may override, if desired.

As discussed above, a predetermined height threshold may be programmed into a patient side cart, which may be a height corresponding to a height of an object. According to an exemplary embodiment, the height may be the height of the object in a room (e.g., operating room) that has the lowest vertical height (e.g., lowest vertical height of objects fixed to a ceiling). When this height is known, a user may simply program the height into the patient side cart, for example, by programming the height into a memory accessible by the controller of the cart. However, when the height is not known or a user wishes to verify the height, the obstacle indication system of a patient side cart may be used to determine the height.

To determine a predetermined height threshold, a user may activate a height determination mode of a patient side cart, according to an exemplary embodiment. In the height determination mode, the obstacle indication device (e.g., laser 540) is activated. The user may then raise or lower boom 506 of patient side cart 500 to determine the height of various objects in a room. For example, a user may orient patient side cart 500 relative to an object 560 in FIG. 7 so laser 540 is illuminating object 560 with light 542, lower boom 506 until light 542 is at the lowest point of object 560 (e.g., end 561), and then store the corresponding vertical height 550 of cart 500 (e.g., by activating a control at steering interface 520), which becomes the stored predetermined height threshold. According to an exemplary embodiment, vertical height 550 is known because the controller actuates and tracks the raising or lowering of boom 506 along directions 530, and therefore knows vertical height 550 as boom 506 is moved. The process of determining a height of an object by using the obstacle indication system may be repeated for a plurality of objects in a room. According to an exemplary embodiment, the controller may select the lowest stored vertical height as the predetermined height threshold from amongst a plurality of stored heights for various objects.

A memory accessible to the controller may include a single predetermined height threshold determined according to the exemplary embodiments described above. According to another exemplary embodiment, the memory may include a stored predetermined height threshold for various rooms or areas. Thus, a user may select a stored predetermined height threshold corresponding to the location of a patient side cart from amongst various predetermined height thresholds, which may have been stored.

A patient side cart may include various measures to account for possible errors related to an obstacle indication system. In the various exemplary embodiments described above, an obstacle indication device may be located at substantially the highest point of a patient side cart. For instance, an obstacle indication device may be located at a highest point mechanically practical. However, due to mechanical constraints, a laser or other obstacle notification device may not be located at the highest point of a patient side cart, which may lead to a relatively small portion of the cart extending above the obstacle detection device that may otherwise not be accounted for. As shown in the exemplary embodiment of FIG. 8, a laser 640 may be located in a boom 606 at a distance 643 below a top surface 603 of boom 606. To account for this, a controller of cart may add distance 643 to a predetermined height threshold stored in cart, which may be used to determine when laser 640 is activated. In this way, the top portion of boom 606 extending above laser 640 may be accounted for.

Another possible error may be due to an obstacle indication device not being oriented along a desired direction. For example, in FIG. 8, laser 640 may be oriented at a non-zero angle 645 relative to a plane 650 (which may be parallel to ground surface 552 in the exemplary embodiment of FIG. 7) instead of emitting light 642 parallel to plane 650. Such an error may be due to, for example, manufacturing tolerances when installing laser 640. To account for this possible error, the controller may set a range about a predetermined height threshold used to determine when to activate an obstacle indication device. According to an exemplary embodiment, the controller may account for an error of, for example, about +/−2° or less about a stored predetermined height or range for an object at a distance of about 3 meters from the cart to account for error due to angle 645. According to another exemplary embodiment, the controller may account for an error of about +/−1° or less about a stored predetermined height or range for an object at a distance of about 3 meters from the cart.

According to another exemplary embodiment, illumination devices may be installed in a patient side cart with an upward bias so that illumination device is oriented at a positive angle 645 relative to plane 650. As a result, the possible error due to an illumination device being oriented at a non-zero angle 645 relative to plane 650 may be ignored because any misalignment is guaranteed to be biased upward, which will ensure that objects illuminated by the illumination device (or height measurements determined with illumination device) will be conservative (e.g., higher than an actual height for the illumination device) and thus facilitate avoiding collisions with obstacles.

As discussed in the exemplary embodiments above, an obstacle indication device may illuminate an object, such as via a laser. However, the various exemplary embodiments described herein are not limited to such devices. For instance, the various exemplary embodiments are not limited to such illumination sources that are passive in nature and only illuminate an object for a user to recognize an obstacle for a potential collision and take corrective action. According to an exemplary embodiment, an obstacle indication system may also be configured to actively detect an object and automatically determine an object to be an obstacle. Exemplary active obstacle indication devices of such a system could be, for example, a lidar (light detection and ranging) device that emits light and detects light scattered by an object in the path of a patient side cart; an ultrasonic range finder, which may determine the presence of an obstacle, as well as its distance from a patient side cart, by emitting an ultrasonic pulse that is reflected from an object; an optical infrared ranging device that emits and detects infrared radiation reflected from an object; a camera providing an image that is analyzed by a controller to detect an object in the image; or other types of active obstacle indication devices familiar to one of ordinary skill in the art. According to an exemplary embodiment, the controller of a patient side cart may receive a detection signal from the active obstacle indication device and determine that the detected object is an obstacle. According to another exemplary embodiment, an active obstacle indication device may be a collision detection device (which may be, for example, mounted on a patient side cart boom), such as, for example, a contact switch, a resistive touch sensor, an accelerometer, a force or torque sensor, or other type of sensor to detect a collision between the patient side cart and an object. Active obstacle indication devices may be used with the various exemplary embodiments described herein.

Although the various exemplary embodiments described herein may use an illumination device emitting light spanning the angle 446 of the exemplary embodiment of FIG. 5, illumination devices may be used that emit light over differing ranges. For example, illumination devices may be used that emit light spanning an angle of, for example, up to 240 degrees. Further, although light emitted from an illumination device may be symmetrical with respect to a longitudinal axis of a boom, as indicated in the exemplary embodiment of FIG. 5, illumination devices may be configured to emit light spanning an angular range that is asymmetrical with respect to the longitudinal axis of the boom over an angular range according to the various exemplary embodiments described herein.

Figure 9:
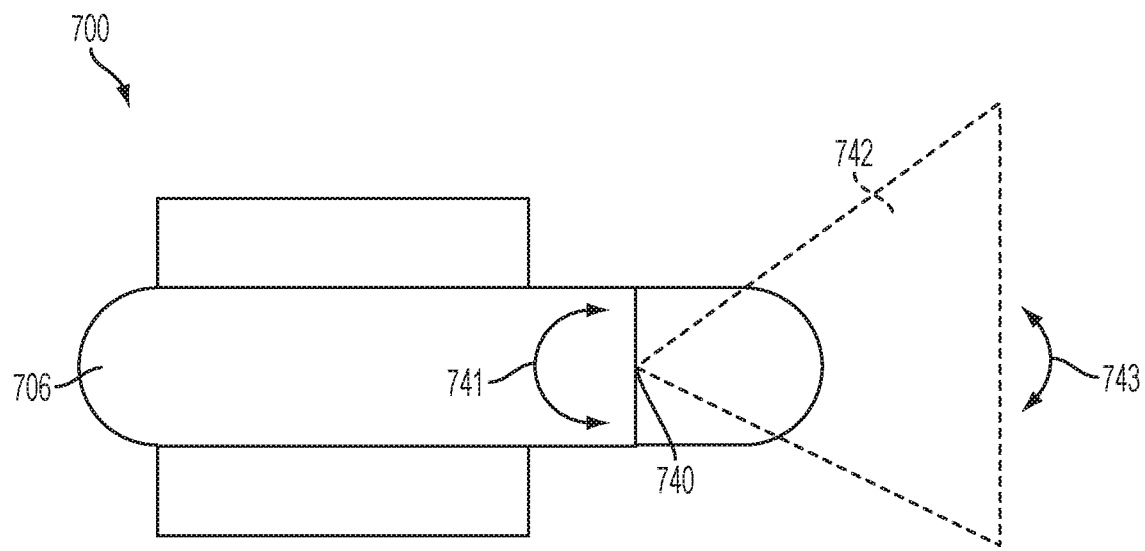
FIG. 9 is a top schematic view of a patient side cart emitting light in a sweeping manner, according to an exemplary embodiment.

An illumination device of the various exemplary embodiments described herein may be stationary with respect to a patient side cart. In another exemplary embodiment, an illumination device of the various exemplary embodiments described herein may move with respect to a patient side cart. As shown in FIG. 9, which schematically depicts a top view of a patient side cart 700, an illumination device 740 (which may be a laser or other type of passive or active illumination device of the various exemplary embodiments described herein) may be configured to move with respect to a boom 706 of patient side cart 700. Patient side cart 700 may be arranged, for example, according to the exemplary embodiments of FIGS. 1 and 2. According to an exemplary embodiment, illumination device 740 itself may be configured to pivot or rotate along direction 741 with respect to boom 706 so that light 742 emitted by illumination device 740 sweeps along directions 743. Illumination device 740 may include, for example, one or more motors or other type of actuator to pivot illumination device 740 with respect to boom 706. According to another exemplary embodiment, illumination device 740 may be stationary with respect to boom 706 but include mirrors (not shown) or other devices that cause light 742 to sweep along directions 743. By sweeping light 742 along directions 743 according to the above embodiments, light 742 may cover a larger region.

Figure 10:
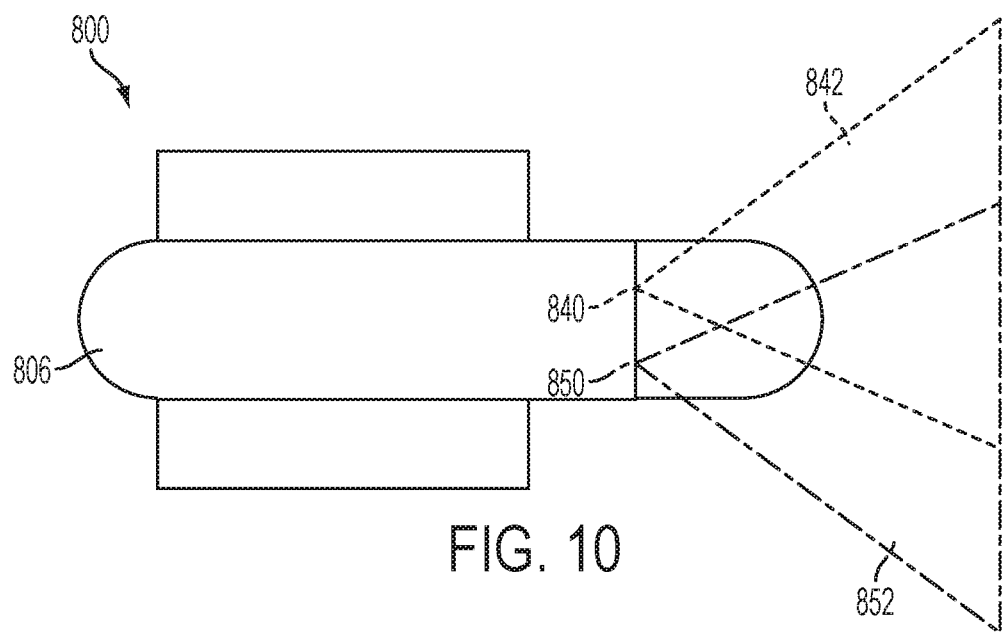
FIG. 10 is a top schematic view of a patient side cart including a plurality of illumination devices, according to an exemplary embodiment.

Patient side carts of the various exemplary embodiments described herein may include a single illumination device, as indicated in the exemplary embodiment of FIG. 5. However, the various exemplary embodiments described herein are not limited to a single illumination device (whether passive or active) and may include a plurality of illumination devices. Turning to FIG. 10, which schematically depicts a top view of a patient side cart 800, a first illumination device 840 emitting light 842 and a second illumination device 850 emitting light 852 may be located in boom 806 of patient side cart 800. Patient side cart 800 may be arranged, for example, according to the exemplary embodiments of FIGS. 1 and 2. Light 842 and 852 may span angular ranges according to the exemplary embodiments described herein, such as with respect to the exemplary embodiment of FIG. 5. Light 842 and 852 emitted by illumination devices 840 and 850 may overlap, as indicated in the exemplary embodiment of FIG. 10, or may be emitted to be adjacent to one another. Thus, light 842 and 852 may cover a larger region to indicate the presence of an obstacle. Although the exemplary embodiment of FIG. 10 shows two illumination devices 840 and 850, other numbers of illumination devices may be used, such as, for example, three, four, five, six, seven, eight, or more illumination devices.

Figure 11:
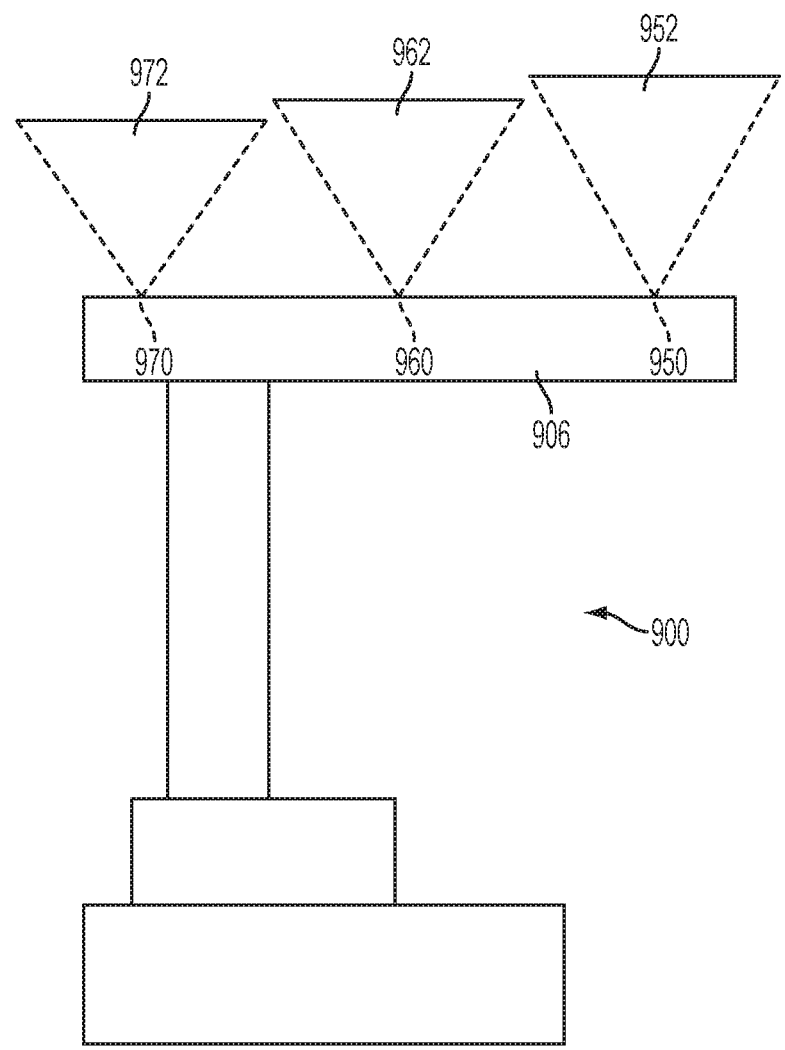
FIG. 11 is a side schematic view of a patient side cart emitting light in a vertical direction, according to an exemplary embodiment.

As indicated in the exemplary embodiments of FIGS. 5, 9, and 10, one or more illumination devices may be used to emit light along a substantially horizontal direction with respect to a surface upon which a patient side cart is located. According to an exemplary embodiment, a patient side cart may include one or more illumination devices (passive or active) to detect objects above the patient side cart, which may be obstacles for when a column of the patient side cart is actuated to raise a boom of the patient side cart. Turning to FIG. 11, a patient side cart 900 is schematically depicted that includes a boom 906 including a plurality of illumination devices 950, 960, 970 that respectively emit light 952, 962, 972 in a vertical direction above boom 906. Illumination devices 950, 960, 970 may be, for example, active devices (such as the active devices described in the various exemplary embodiments above) that automatically detect obstacles above boom 906 and notify a user, or illumination devices 950, 960, 970 may be passive devices (such as a laser or other passive illumination device described in the exemplary embodiments above). Although the exemplary embodiment of FIG. 11 depicts three illumination devices 950, 960, 970, other numbers of illumination devices to emit light in a vertical direction above a patient side cart may be used, such as, for example, one, two, four, five, six, or more illumination devices. Further, the exemplary embodiments described with respect to FIG. 11 may be used in combination with the various exemplary embodiments described herein and may include one or more illumination devices emitting light in a substantially horizontal direction. Patient side cart 900 may be arranged, for example, according to the exemplary embodiments of FIGS. 1 and 2.

Figure 8:
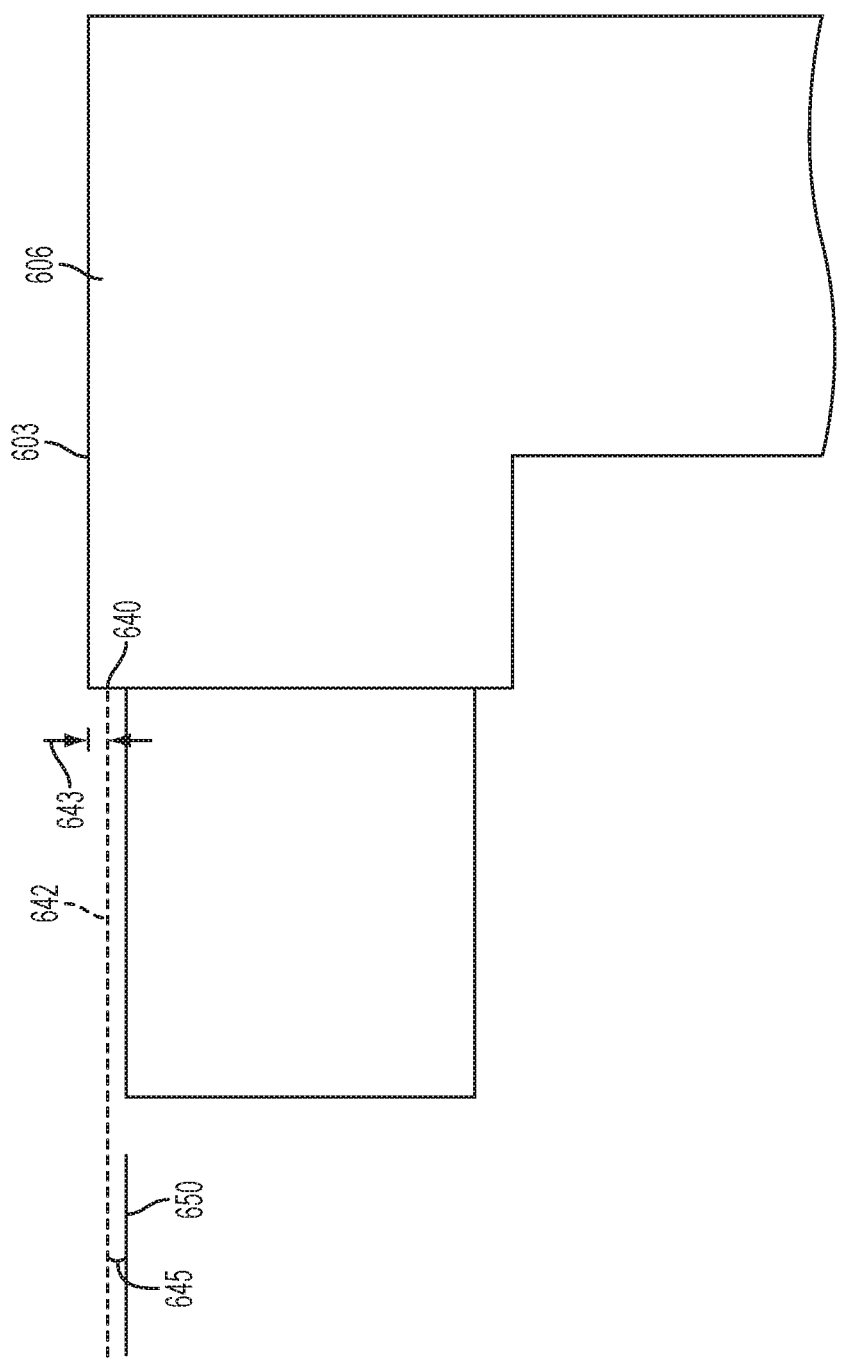
FIG. 8 is a partial schematic side view of a patient side cart boom, according to an exemplary embodiment.
Figure 12:
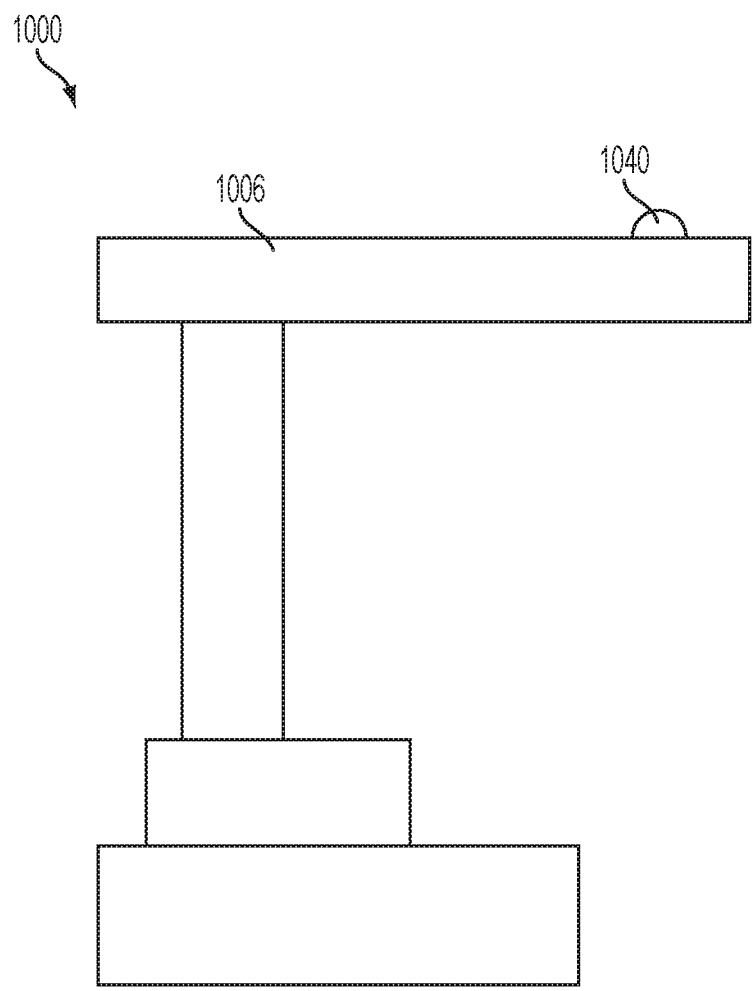
FIG. 12 is a side schematic view of a patient side cart including an illumination device located on top of a boom of the patient side cart, according to an exemplary embodiment.

As described above with respect to the exemplary embodiment of FIG. 8, an obstacle notification device may not be located at the highest point of a patient side cart. Turning to FIG. 12, a patient side cart 1000 is schematically depicted that includes an obstacle notification device 1040 located on top of a boom 1006 so that obstacle notification device 1040 is located at a highest point of patient side cart 1000. Obstacle notification device 1040 may be an illumination device (e.g., passive or active) configured according to the various exemplary embodiments described herein. Patient side cart 1000 may be arranged, for example, according to the exemplary embodiments of FIGS. 1 and 2. According to an exemplary embodiment, obstacle notification device 1040 may emit light over an angular extent described in the exemplary embodiments above, such as, for example, the exemplary embodiment of FIG. 5. However, obstacle notification device 1040 may emit light over other angular extents, such as an angular extent of up to, and including, 360°. For example, obstacle notification device 1040 may be an active obstacle notification device that checks for obstacle over an angular extent of up to, and including, 360° and notifies a user of any objects detected within a range of obstacle notification device 1040 over that angular extent.

Providing a patient side cart with an obstacle recognition device may facilitate recognition of obstacles the patient side cart may collide with, which may in turn minimize or prevent damage to the patient side cart.

Further modifications and alternative embodiments will be apparent to those of ordinary skill in the art in view of the disclosure herein. For example, the devices, systems, and methods may include additional components or steps that were omitted from the diagrams and description for clarity of operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the scope of the present disclosure and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the invention disclosed herein. It is intended that the specification and examples be considered as exemplary only, with being entitled to their full breadth of scope, including equivalents by the following claims.

What is claimed is:

1. A patient side cart for a teleoperated surgical system, the patient side cart comprising:
    a column extending from a base, the column having a first end connected to the base and a second end opposite the first end;
    a surgical instrument manipulator arm coupled proximate the second end of the column; and
    an obstacle indication system comprising an illumination source mounted on the patient side cart at a height above a location the surgical instrument manipulator arm is coupled to the second end of the column, the height being measured in a direction the column extends from the base.

2. The patient side cart of claim 1, further comprising:
    a memory storing a threshold height, the threshold height being set based on illumination of an obstacle with the illumination source.

3. The patient side cart of claim 2, wherein the illumination source is automatically activated in response to a height of the patient side cart being equal to or exceeding the threshold height stored in the memory.

4. The patient side cart of claim 2, wherein the illumination source is automatically activated in response to a height of the patient side cart being equal to or exceeding a height that is less than the threshold height stored in the memory.

5. The patient side cart of claim 4, wherein the illumination source is automatically activated in response to a height of the patient side cart being equal to or exceeding about 80% of the threshold height stored in the memory.

6. The patient side cart of claim 1, wherein the illumination source is a laser.

7. The patient side cart of claim 6, wherein light from the laser spans an angular range.

8. The patient side cart of claim 1, wherein the illumination source is automatically activated in response to translation of the patient side cart from one location to another on a surface supporting the patient side cart.

9. The patient side cart of claim 1, wherein the column is configured to extend away from the base and to retract toward the base.

10. The patient side cart of claim 9, wherein the illumination source is automatically activated in response to the column extending or retracting.

11. A method of operating a patient side cart for a teleoperated surgical system, the method comprising:
    illuminating an obstacle with light from an illumination source mounted on the patient side cart;
    in response to the illuminating, storing a threshold height in a memory of the patient side cart; and
    automatically controlling a motion of the patient side cart based on the threshold height.

12. The method of claim 11, wherein:
    the patient side cart comprises a base, a column extending from the base, and a surgical instrument manipulator arm coupled to the column; and
    illuminating the obstacle with light from the illumination source mounted on the patient side cart comprises illuminating the obstacle with light from an illumination source mounted on the patient side cart at a height above a location at which the surgical instrument manipulator arm is coupled to the column, the height being measured in a direction the column extends from the base.

13. The method of claim 11, wherein a height of the patient side cart is adjustable, the method further comprising:
    automatically preventing adjusting the height of the patient side cart from exceeding the threshold height.

14. The method of claim 11, wherein a height of the patient side cart is adjustable, the method further comprising:
    automatically preventing adjusting the height of the patient side cart from exceeding a height less than the threshold height.

15. The method of claim 14, wherein the automatically preventing adjusting the height of the patient side cart from exceeding a height less than the threshold height comprises automatically preventing adjusting the height of the patient side cart from exceeding a height that is about 80% of the threshold height.

16. The method of claim 11, wherein a height of the patient side cart is adjustable, the method further comprising:
   automatically preventing adjusting the height of the patient side cart from exceeding a height within a predetermined range of the threshold height.

17. The method of claim 11, wherein the obstacle is a first obstacle, the threshold height is a first threshold height, and a height of the patient side cart is adjustable, the method further comprising:
   illuminating a second obstacle with light from the illumination source mounted on the patient side cart;
   in response to the illuminating of the second obstacle, storing a second threshold height in the memory of the patient side cart; and
   automatically preventing adjusting the height of the patient side cart from exceeding a lower one of the first threshold height and the second threshold height.

18. The method of claim 11, wherein the obstacle is a first obstacle, the threshold height is a first threshold height, and a height of the patient side cart is adjustable, the method further comprising:
   illuminating a second obstacle with light from the illumination source mounted on the patient side cart;
   in response to the illuminating of the second obstacle, storing a second threshold height in the memory of the patient side cart; and
   automatically preventing adjusting the height of the patient side cart from exceeding a combination of a limit height and range of height beyond the limit height, the limit height being a lower one of the first threshold height and the second threshold height.

19. The method of claim 11, further comprising:
automatically preventing a translating movement of the patient side cart during a condition of a height of the patient side cart exceeding the threshold height.

20. The method of claim 19, further comprising:
generating an indication to a user, in response to automatically preventing a translating movement of the patient side cart; and
enabling the translating movement of the patient side cart on the condition of the user acknowledging the indication.

21. The method of claim 11, further comprising:
automatically preventing a translating movement of the patient side cart during a condition of a height of the patient side cart being within a predetermined range of the threshold height.

22. The method of claim 21, further comprising:
generating an indication to a user, in response to automatically preventing a translating movement of the patient side cart; and
enabling the translating movement of the patient side cart on the condition of the user acknowledging the indication.

\* \* \* \* \*